(12) United States Patent
Darling et al.

(10) Patent No.: US 6,200,622 B1
(45) Date of Patent: Mar. 13, 2001

(54) FROZEN FOOD PRODUCT

(75) Inventors: Donald Frank Darling; Andrew Hoddle, both of Colworth (GB)

(73) Assignee: Good Humor - Breyers Ice Cream, division of Conopco, Green Bay, WI (US)

( * ) Notice: Subject to any disclaimer, the term of this patent is extended or adjusted under 35 U.S.C. 154(b) by 0 days.

(21) Appl. No.: 09/042,056

(22) Filed: Mar. 13, 1998

(30) Foreign Application Priority Data

Mar. 14, 1997 (GB) ................................................ 97301733

(51) Int. Cl.⁷ .............................. A23G 9/00; C07K 1/00; C07K 14/00; A23B 7/10
(52) U.S. Cl. .......................... 426/565; 426/524; 426/656; 426/660; 426/101; 530/350
(58) Field of Search ...................................... 426/524, 565, 426/49, 656, 660, 100, 101; 530/350, 326, 328, 300

(56) References Cited

U.S. PATENT DOCUMENTS

| | | | |
|---|---|---|---|
| 4,476,248 | * 10/1984 | Gordon et al. | 562/494 |
| 4,565,643 | * 1/1986 | Arai et al. | 252/70 |
| 4,710,231 | * 12/1987 | Bateman et al. | 127/30 |
| 5,118,792 | * 6/1992 | Warren et al. | 530/350 |
| 5,194,269 | * 3/1993 | Lee | 426/61 |
| 5,215,777 | * 6/1993 | Asher et al. | 426/565 |
| 5,620,732 | * 4/1997 | Clemmings et al. | 426/565 |
| 5,676,985 | * 10/1997 | Fletcher | 426/36 |
| 5,849,333 | * 12/1998 | Nordhauser et al. | 424/489 |
| 5,849,537 | * 12/1998 | Tripp et al. | 435/69.7 |
| 5,852,172 | * 12/1998 | Griffith | 530/379 |
| 6,017,574 | * 1/2000 | Clemmings et al. | . |
| 6,090,917 | * 8/2000 | Lillford et al. | . |
| 6,096,867 | * 8/2000 | Byass et al. | . |

FOREIGN PATENT DOCUMENTS

| | | |
|---|---|---|
| 90/13571 | 11/1990 | (WO) . |
| 92/22581 | 12/1992 | (WO) . |
| 94/03617 | 2/1994 | (WO) . |
| 96/39878 | 12/1996 | (WO) . |
| 97/02343 | 1/1997 | (WO) . |
| 97/03634 | 2/1997 | (WO) . |
| 97/03635 | 2/1997 | (WO) . |
| 97/03636 | 2/1997 | (WO) . |
| 97/06181 | 2/1997 | (WO) . |

OTHER PUBLICATIONS

Perry's Chemical Engineers' Handbook, 6th Edition, pp. 8–6, 8–7, 1984.*

Arbickle, "Ice Cream", 3$^{rd}$ Edition, pp. 246, 323–330, 1977.*

Griffith et al, "Antifreeze Proteins and Their Potential Use in Frozen Foods", Biotechnology Advances, vol. 13, No. 3 p. 375–402, 1995.*

Feeney et al., *Antifreeze Proteins: Properties, Mechanism of Action, and Possible Applications*, 156 Food Technology, Jan. 1993, p. 82–89, cited on p. 1 of the specification.

* cited by examiner

*Primary Examiner*—Cynthia L. Nessler
(74) *Attorney, Agent, or Firm*—James J. Farrell

(57) ABSTRACT

A process for the production of a frozen food product comprising anti-freeze peptide (AFP), wherein the product is at least partially pre-frozen in the substantial absence of free AFP, followed by including the free AFP therein.

4 Claims, No Drawings

FROZEN FOOD PRODUCT

TECHNICAL FIELD OF THE INVENTION

The invention relates to a process for the preparation of a food product containing AFPs and to food products containing AFPs.

BACKGROUND TO THE INVENTION

Anti-freeze peptides (AFPs) have been suggested for improving the freezing tolerance of foodstuffs. For the purpose of this invention the term AFP has the meaning such as well-known in the art, see for example "Antifreeze proteins and their potential use in frozen food products", Marilyn Griffiths et al. Biotechnology Advances, Vol.13, pp.375–402, 1995

WO 90/13571 discloses antifreeze peptides produced chemically or by recombinant DNA techniques from plants. The AFPs can suitably be used in food-products such as ice-cream.

WO 92/22581 discloses AFPs from plants which can be used for controlling ice crystal growth in ice-cream. This document also describes a process for extracting a polypeptide composition from intercellular spaces of plants by infiltrating leaves with an extraction medium without rupturing the plant cells.

WO 94/03617 discloses the production of AFPs from yeast and their possible use in ice-cream. WO 96/11586 describes fish AFPs produced by microbes.

Up till now, however the use of AFPs has not been applied to commercially available food products. One reason for this is that up till now it has proved difficult to reproducibly produce a frozen food product having the desired texture and eating characteristics.

The present invention aims at providing solutions to these problems. In particular the invention aims at providing frozen food products containing AFPs and having a non-brittle texture, said texture being maintained upon prolonged storage at low temperatures.

PCT/EP97/03635 (non-pre-published) relates to the production of frozen food products containing AFPs and having a relatively hard and brittle texture by adapting the aspect ratio of the ice-crystals in the product.

PCT/EP97/03636 (non-pre-published) relates to the production of frozen food products containing AFPs and having a relatively soft although brittle texture by adapting the aspect ratio of the ice-crystals in the product.

Surprisingly it has been found that it is possible to obtain frozen food products containing AFPs which are non-brittle, provided the process of producing the AFP containing product is carefully selected.

Accordingly in a first aspect, the invention relates to a process for the production of a frozen food product comprising AFP, wherein the product is at least partially pre-frozen in the substantial absence of free AFP, followed by including the free AFP therein.

Without being bound by any theory applicants believe that the favourable textural properties of the product can be explained as follows: If food products are pre-frozen, ice-crystals are formed throughout the product. If free AFPs become thereafter available in the pre-frozen products this generally leads to a maintenance of the shape and size of the initially formed crystals even if the product is subjected to temperature changes during storage. However the presence of the free AFPs only at a late stage of the freezing process, i.e. after at least part of the ice-crystals have been formed, seems to lead to a reduction of aggregation between the ice-crystals of the final product, therewith resulting in a less brittle product.

For the purpose of the invention the term free AFP encompasses all forms of AFP which can interact with the ice-crystals. The absence of free AFP means that either no AFP is present in the system or AFP is present in a form such that it cannot interact with the ice-crystals. The presence of free AFP can be shown by using the recrystallisation inhibition test such as illustrated in the examples.

Many consumers are in favour of less brittle frozen food products or ingredients such as ice-cream or water-ice.

Surprisingly we have found that AFPs offer the opportunity to formulate frozen food products which on the one hand are less brittle and on the other hand retain improved ice-recrystallisation and temperature tolerance properties upon storage abuse.

Products according to the invention are characterised by a significantly lower Brinell hardness, than products with the same composition, wherein free AFP is present before freezing. Preferably at $-18°$ C. the force (in N) at a displacement of 2 mm measured as in the examples for products where the free AFP is present prior to (partial) freezing is at least 1.5 times the force (in N) for the same composition wherein free AFP is present only after (partial) prefreezing. More preferably the force is from 2.0 to 4.0 times the force of products of the invention. The force for products of the invention and measured as indicated above is preferably from 5 to 100 N, more general from 7 to 40 N, more specifically from 10 to 30 N.

The aspect ratio of ice-crystals in compositions produced according to the process of the invention is preferably less than 2.0, e.g. from 1.0 to 1.9. The aspect ratio of ice-crystals is defined as the average ratio of the length and the breadth of the ice-crystals. An aspect ratio of less than 2.0 corresponds to roundish ice-crystals, which are not elongated in shape. The aspect ratio of crystals can be determined by any suitable method. A preferred method is illustrated in the examples.

Preferably the frozen product of the invention are non-brittle. Preferably the minimum layer thickness at which fracture behaviour can be observed is more than 10 mm, more preferred more than 50 mm. Fracture behaviour can either be measured by preparing layers of varying thickness and determining at which minimum thickness fracture behaviour occurs or calculated from the Young Modulus as described in the examples.

During the formulation and subsequent freezing of food products several parameters can influence the aspect ratio of the ice-crystals to be formed. Examples of factors influencing the aspect ratio are given below. Applicants believe that it is well-within the ability of the skilled person to choose those conditions such that the aspect ratio of the ice-crystals falls within the desired range.

One factor influencing the aspect ratio of ice-crystals is the rate of freezing the product. Generally speaking an increase of the rate of freezing may lead to a decrease in the aspect ratio for the ice-crystals.

Another factor influencing the aspect ratio of ice-crystals is the mobility of the product during freezing. For example if a liquid water-ice or ice-cream mix is to be frozen, quiescently freezing will lead to a fairly high aspect ratio for the ice-crystals, while stirring leads to a lower aspect ratio. High shear mixing will lead to even lower aspect ratios.

Another factor to influence the aspect ratio of the ice crystals is the presence and amounts of ingredients. For example the presence of ingredients which tend to form a network structure in the product (e.g. gums or fats) may lead to a lower aspect ratio than in products without these ingredients. Also other ingredients may lead to lower aspect ratios, for example high solids levels e.g. high sugar levels may lead to low aspect ratios. Also high phase volumes for the ice may lead to higher aspect ratios.

Finally the nature and amount of the AFPs present may lead to a change in aspect ratios. Some AFPs seem to favour the formation of low aspect ratios, while other AFPs seem to induce higher aspect ratios. Variation in the amount of AFPs may lead to a change in aspect ratios.

The process of the invention involves at least the partial pre-freezing of the product prior to the presence of free AFP. This partial prefreezing preferably freezes at least 20 wt % of the water present in the pre-mix, e.g. from 30–100 wt %, preferably 40–80 wt %. This pre-freezing can be done by any suitable method. Particularly preferred however is the partial pre-freezing in a device wherein freezing and aeration (if desired) takes place at the same time. Suitable devices for this are for example scraped surface heat exchangers, wherein the food product is pre-frozen e.g. to a temperature of between −2 and −6° C.

In a first embodiment of the invention the pre-freezing takes place in the absence of AFP. After pre-freezing the free AFP is then made available e.g. by addition to the prefrozen product e.g. by mixing a solution of AFP into the pre-frozen product, for example by means of mixing in a static mixer. Alternatively the mix to be frozen can be split in two or more streams, whereby at least one of the streams, which is free from AFP, is prefrozen and subsequently mixed with the remaining stream(s) comprising the AFP. Another suitable embodiment involves the use of two or more freezers in sequence, whereby the AFP is added to the system between two freezers.

In a second embodiment of the invention the pre-freezing takes place in the presence of non-free AFP. After the prefreezing the AFP is made available e.g. by ensuring that the non-free AFP is released in free form. This can for example be achieved by varying the processing conditions such that AFP encapsulates are opened to release the AFP. Alternatively complexes wherein the AFP is present in non-free form may be changed such that free AFP is released.

As indicated above the AFP can be added in several forms.

If the AFP is added in free form e.g. as such or in solution or as part of a product stream then according to the invention it will be added after at least partially prefreezing the product.

If the AFP is added in non-free form then the AFP may also be added before partial prefreezing as long as the nature of the AFP system and the processing conditions are chosen such that substantially no free AFP becomes available before (partial) pre-freezing.

In a very preferred embodiment of the invention the AFP is brought into non-free form by inclusion into gelled particles. Any gelling agent may be used. Preferably the strength of the gel is chosen such that under normal shear conditions in the freezer the gels break whereby the AFP is released in free form. Suitable gels may for example be based on edible gelling agents such as alginate, iota or kappa carrageenan, gellan, agar, pectin, furcelleran, guar gum, locust bean gum, especially preferably are alginate gels.

Preferably the gel strength of the gels, the particle size and shape are chosen such that the gelled particles are broken during the freezing process. Generally gel strength can be varied by varying the amount of gelling agent. Also irregularly shaped particles will be more easily disrupted than round particles. It will be within the scope of the skilled person to design those conditions which will lead to the desired particles.

An alternative form of non-free AFP relates to the incorporation of the AFP in liquid crystal structures for example in liposomes whereby the liposomes are chosen such that the AFP is released in free form after the partial prefreezing of the product. Suitable liposome structures may for example be based on edible surfactant materials e.g. mono- or di-glycerides.

Other techniques may also be used to prepare non-free AFP. Examples of these are encapsulated AFP, inclusion of AFPs in emulsion systems etc.

After the free AFP becomes available in the prefrozen product, the product can optionally be further handled e.g. it can be further frozen (post-hardened e.g. to a temperature of less than −18° C.), other ingredients can be added, the product can be packed, shaped, extruded etc.

Preferably however the temperature of the product after the free AFP becomes available will not be so high that a most of the ice-crystals will melt.

The process of the invention can be applied to any frozen food product containing AFPs. Examples of frozen food products which may contain AFP are processed food products such as for example frozen bakery products e.g. doughs, batters, cakes etc., frozen culinary products for example soups, sauces, pizzas, frozen vegetable products such as compote, mashed potato, tomato paste etc. A very preferred food product according to the invention is a frozen confectionery product.

For the purpose of the invention the term frozen confectionery product includes milk containing frozen confections such as ice-cream, frozen yoghurt, sherbet, sorbet, ice milk and frozen custard, water-ices, granitas and frozen fruit purees. Especially preferred products of the invention are ice-cream and water-ice.

Applicants have found that the AFPs for use in the process of the invention can come from a variety of sources such as plants, fishes, insects and micro-organisms. Both natural occurring species may be used or species which have been obtained through genetic modification. For example microorganisms or plants may be genetically modified to express AFPs and the AFPs may then be used in accordance to the present invention.

Genetic manipulation techniques may be used to produce AFPs as follows: An appropriate host cell or organism would be transformed by a gene construct that contains the desired polypeptide. The nucleotide sequence coding for the polypeptide can be inserted into a suitable expression vector encoding the necessary elements for transcription and translation and in such a manner that they will be expressed under appropriate conditions (e.g. in proper orientation and correct reading frame and with appropriate targeting and expression sequences). The methods required to construct these expression vectors are well known to those skilled in the art.

A number of expression systems may be utilised to express the polypeptide coding sequence. These include, but are not limited to, bacteria, yeast insect cell systems, plant cell culture systems and plants all transformed with the appropriate expression vectors.

A wide variety of plants and plant cell systems can be transformed with the nucleic acid constructs of the desired polypeptides. Preferred embodiments would include, but are not limited to, maize, tomato, tobacco, carrots, strawberries, rape seed and sugar beet.

For the purpose of the invention one set of preferred AFPs are derived from fish. Especially preferred is the use of fish proteins of the type III, most preferred HPLC 12 as described in our case WO97/02343. Another preferred AFP can be derived from vegetable sources such as grass or winter-rye as described in our non-prepublished case PCT/EP97/03634 or carrot as described in our non-prepublished application PCT/EP97/06181. Especially preferred is the use of plant AFPs.

For some natural sources the AFPs may consist of a mixture of two or more different AFPs.

Preferably those AFPs are chosen which have significant ice-recrystallisation inhibition properties, this can be measured in line with the examples.

As indicated above the preferred frozen products wherein the AFPs are used are frozen confectionery product such as ice-cream or water-ice. Preferably the level of AFPs is from 0.0001 to 0.5 wt % based on the final product.

Surprisingly it has been found that compositions of the invention can contain very low amounts of AFPs while still being of good quality.

Preferably the level of solids in the frozen confection (e.g. sugar, fat, flavouring etc.) is more than 3 wt %, more preferred from 4 to 70 wt %.

EXAMPLE I

Ice-cream was prepared of the following formulations:

| Ingredient % by weight | A | B | C |
|---|---|---|---|
| Skimmed milk powder | 10.00 | 10.00 | 10.00 |
| Sucrose | 13.00 | 13.00 | 13.00 |
| Maltodextrine (MD40) | 4.00 | 4.00 | 4.00 |
| Locust bean gum | 0.14 | 0.14 | 0.14 |
| Butter oil | 8.00 | 8.00 | 8.00 |
| Monoglyceride (palmitate) | 0.30 | 0.30 | 0.30 |
| Vanillin | 0.01 | 0.01 | 0.01 |
| AFP (Type III HPLC-12) | 0.005 | 0.005 | none |
| Water | Balance | Balance | Balance |

Note:
AFP Type III HPLC-12 is described in WO 97/023,343

The method of preparation was as follows: For compositions B and C (comparison) all ingredients were mixed and frozen in a scraped surface heat exchanger to an extrusion temperature of −6.1° C. and an overrun of 94% (B) or 113% (C), followed by post-hardening to −35° C. in a conventional blast freezer. Composition A was mixed and pre-frozen as the other compositions, but after extrusion the AFP was post added and homogeneously mixed into the product in a static mixer. The product has an overrun of 96%. At the extrusion temperature the product contained about 40 wt % of ice corresponding to about 60% of the water being frozen. After the mixing of the AFP product A was also post-hardened to a temperature of −35° C. in a blast freezer.

The products were subjected to storage abuse by keeping them at −10° C. for a period of 10 days.

Samples of the products were equilibrated at −18° C. in a Prolan environmental cabinet for approximately 12 hours. Microscopic slides were prepared by smearing a thin layer of ice-cream from the centre of thin glass plates.

Each slide was transferred to a temperature controlled microscopic stage (at −18° C.) where images of ice-crystals (about 400 individual ice-crystals) were collected and relayed through a video camera to an image storage and analysis system.

The stored ice crystal images were highlighted manually by drawing around its perimeter which then highlights the whole crystal. Images of the highlighted crystals were then measured using the image analysis software which counts the number of pixels required to complete the longest straight line (length), shortest straight line (breadth), the aspect ratio (length/breadth).

The average aspect ratio for the crystals was calculated.
The following results were obtained:

TABLE 1

| Process stage | ICS | A | B | C |
|---|---|---|---|---|
| Extrusion | Length (µm) | 15.1 | 18.3 | 13 |
|  | Breadth (µm) | 9.4 | 7.0 | 8.1 |
|  | Aspect Ratio | 1.6 | 2.7 | 1.7 |
| Hardened | Length (µm) | 35.1 | 32.4 | 34.3 |
|  | Breadth (µm) | 22.9 | 14.4 | 24.9 |
|  | Aspect Ratio | 1.6 | 2.3 | 1.4 |
| Storage Abused | Length (µm) | 37.9 | 35 | 51.4 |
|  | Breadth (µm) | 23 | 15.5 | 35 |
|  | Aspect Ratio | 1.6 | 2.3 | 1.5 |

The hardness of the hardened samples (before storage abuse) was tested by a Brinell Hardness test, whereby ice-cream samples (at −18° C.) are inserted in a Instron Universal tester and a spherical ball (diameter 15 mm) is pushed into the ice-cream at a constant rate (5 mm/min) and the resistance to movement is measured. For sample A the force at a displacement of 2 mm is about 18 N, For sample B the force was about 47 N. For C about 15 N.

EXAMPLE II

The brittleness of the ice-creams of example I can be determined by calculations on the fracture behaviour of the ice-cream. Using a 3-Point bend test the Young Modulus was measured.

The Young modulus can be measured by preparing strips of ice-cream, equilibrating them for 18 hours in a freezer cabinet and transferring to a temperature cabinet. The strips are placed on a 3-point bend rig as described in *Handbook of Plastics Test Methods* (2nd Edition), ed R. P. Brown, George Godwin Ltd, 1981. Sample testing is carried out immediately at a deformation speed of 50 m/min. From the force-deformation curve, the initial slope is measured and used to calculate the Young modulus according to the following equation:

$$\text{Young Modulus (Pa)} = \frac{\text{Slope} \cdot L^3}{4 \cdot B \cdot W^3}$$

where L=beam span (110 mm), B=sample width, W=sample height. Usually eight samples were tested to give a mean Young's Modulus value.

Using the calculations described by Williams & Cawood in Polymer Testing 9 15–26 (1990) the fracture toughness can be calculated.

The results are as follows: Composition A (according to the invention) has a significantly lower brittleness than composition B and a comparable brittleness to composition C.

EXAMPLE III

Examples I and II can be repeated by using instead of fish AFP 4 wt % of AFP containing carrot juice obtained by scrubbing freshly pulled cold acclimatised carrots in water. The tops are removed and the juice extracted using a domestic juice extractor. The carrot juice is used as the source of AFPs instead of fish AFP HPLC12.

EXAMPLE IV

Examples I and II can be repeated by using 0.015 wt % of winter rye AFPs as the source of AFPs instead of fish AFP HPLC12.

The winter rye is cut in January (mean temperature 3.5° C.), the tissue is rapidly transported into the laboratory for further handling and washed thoroughly with water to remove dirt. 400 g of the clippings are homogenised in a Warren blender with 800 g water until the tissue was completely disrupted. The AFP rich juice is collected by filtering through 4 layers of muslin. The juice is boiled for 10 minutes. The supernatant is separated from the precipitate by centrifuging at 15,000 for 20 minutes. The AFP can then be isolated by freeze-drying.

EXAMPLE V

The ice recrystallisation inhibition properties of the AFPs can determined as follows:

A sample of an AFP containing product was adjusted to a sucrose level of 30 wt % (If the starting level of the sample was more than 30% this was done by dilution, if the starting level was lower sucrose was added to the 30% level).

A 3 $\mu$L drop of the sample was placed on a 22 mm coverslip. A 16 mm diameter cover-slip was then placed on top and a 200 g weight was placed on the sample to ensure a uniform slide thickness. The edges of the coverslip were sealed with clear nail varnish.

The slide was placed on a Linkham THM 600 temperature controlled microscope stage. The stage was cooled rapidly (50° C. per minute) to −40° C. to produce a large population of small crystals. The stage temperature was then raised rapidly (50° C. per minute) to −6° C. and held at this temperature.

The ice-phase was observed at −6° C. using a Leica Aristoplan microscope. Polarised light conditions in conjunction with a lambda plate were used to enhance the contrast of the ice crystals. The state of the ice phase (size of ice crystals) was recorded by 35 mm photomicrography at T=0 and T=1 hour. The ice-crystal size (length) was determined by drawing around the perimeter of the crystals. The maximum length for each individual ice crystal of a batch of ice cream was imported into a spreadsheet where analysis of the data set was carried out to find the mean, and standard deviation.

Generally this test can be applied to any suitable composition comprising AFP and water. Generally the level of AFP in such a test composition is not very critical and can for example be from 0.0001 to 0.5 wt %, more preferred 0.0005 to 0.1 wt %, most preferred 0.001 to 0.05 wt %, for example 0.01 wt %

Any suitable composition comprising AFP and water can be used to carry out the test. Generally, however, it will not be necessary to obtain the AFP in purified form. For practical applications normally it would suffice to prepare a liquid extract or juice of natural material, wherein this extract or juice can then be tested.

The above recrystallisation test can be used to determine if AFPs have adequate ice recrystallisation inhibition properties. For this purpose good recrystallisation inhibition properties are evidenced by a (number average) length of the ice-crystals of less than 15 $\mu$m, for example 5–15 $\mu$m.

The above recrystallisation test can also be used to check whether free AFP is present in the system. If AFP is present in free form the above test will normally show a (number average) length of the ice-crystals of less than 15 $\mu$m, for example 5–15 $\mu$m. If the system is free of AFPs or only contains AFPs in non-free form the length will normally be more than 15 $\mu$m, for example 25 $\mu$m or more.

EXAMPLE VI

Ice cream of the following formulations was prepared.

K: Composition C of example I (comparison)

L: Composition C of example I including 10% of alginate beads (see below) and correspondingly less water (comparison)

M: Composition B of example I including 10% of alginate beads (see below) and correspondingly less water (comparison)

N: Composition C of example I including 10% of AFP containing Alginate beads (see below) and correspondingly less water (according to the invention).

Alginate beads were made by dripping 0.333 wt % sodium alginate solution into a 0.123 wt % CaCl$_2$ solution.

AFP containing alginate beads were made by dripping a solution of 0.333 wt % sodium alginate and 0.05 wt % AFP (type III HPLC-12) into a 0.123 wt % CaCl$_2$ solution.

The CaCl$_2$ solutions were well stirred and drop size of the alginate beads was controlled by spraying with an aerosol spray gun with an air blower arranged to ensure that the drops are blown away before they grow too large.

Compositions K–N were frozen in a scraped surface heat exchanger to an extrusion temperature of about −5.4° C. and an overrun of about 97%. During the freezing process the alginate beads disintegrated.

The average length, breadth, and aspect ratio of the formulations was measured (in accordance to example I) after extrusion and hardening to −25° C.

The Brinell hardness of the samples was measured in accordance to example I.

The results are as follows:

| Composition   | K    | L    | M    | N    |
| --- | --- | --- | --- | --- |
| Length ($\mu$m)  | 34.6 | 35.5 | 21.3 | 23.1 |
| Breadth ($\mu$m) | 24.7 | 26.2 | 12.3 | 16.2 |
| aspect ratio  | 1.40 | 1.36 | 1.73 | 1.42 |

Hardness measurements showed that compositions M and N were harder than compositions K and L. However composition N was significantly less hard than composition M.

These results show that if AFP is added in such a form that it is released only after partial pre-freezing has taken place (Composition N) it provides crystal shapes (aspect ratio) similar to compositions without AFP (compositions K and L). The aspect ratio however of composition N was significantly lower than the aspect ratio of composition M wherein the AFP was present in free form before the on-set of the freezing process. Compositions M and N both had advantageous small crystal sizes, however composition N was advantageous in that it had clearly a reduced hardness as compared to formulation M.

What is claimed is:

1. A process for the production of a frozen food product comprising anti-freeze peptide, wherein the food product is frozen in the substantial absence of free anti-freeze peptide to form an at least partially frozen food product wherein at least 20% of the water in the pre-mix is frozen, and contacting the at least partially frozen food product with free anti-freeze peptide.

2. A process according to claim 1 wherein the anti-freeze peptide is added to the product in non-free form by including the anti-freeze peptide into gelled particles, wherein after the, at least partial freezing, the anti-freeze peptide is released in free form from the gelled particles.

3. A process according to claim 1, wherein the level of anti-freeze peptide is from 0.0001 to 0.5 wt % based on the final product.

4. A process according to claim 1, wherein the frozen product is a frozen confectionery product.

* * * * *